United States Patent
Yoshida et al.

(10) Patent No.: US 11,913,885 B2
(45) Date of Patent: Feb. 27, 2024

(54) METHOD AND APPARATUS FOR CALCULATING ABUNDANCE OF SPECIFIC SPECIES OF PHYTOPLANKTON, AND METHOD AND APPARATUS FOR DETECTING SIGN OF RED TIDE OCCURRENCE CAUSED BY SPECIFIC SPECIES OF PHYTOPLANKTON

(71) Applicant: JFE Advantech Co., Ltd., Hyogo (JP)

(72) Inventors: Mitsuo Yoshida, Nishinomiya (JP); Hiroharu Kato, Nishinomiya (JP)

(73) Assignee: JFE ADVANTECH CO., LTD., Hyogo (JP)

( * ) Notice: Subject to any disclaimer, the term of this patent is extended or adjusted under 35 U.S.C. 154(b) by 311 days.

(21) Appl. No.: 17/598,420

(22) PCT Filed: Feb. 20, 2020

(86) PCT No.: PCT/JP2020/006889
§ 371 (c)(1),
(2) Date: Sep. 27, 2021

(87) PCT Pub. No.: WO2020/195412
PCT Pub. Date: Oct. 1, 2020

(65) Prior Publication Data
US 2022/0163451 A1 May 26, 2022

(30) Foreign Application Priority Data
Mar. 27, 2019 (JP) .................. 2019-061670

(51) Int. Cl.
*G01N 21/64* (2006.01)
*A01K 61/13* (2017.01)

(52) U.S. Cl.
CPC .......... *G01N 21/6486* (2013.01); *A01K 61/13* (2017.01); *G01N 2201/062* (2013.01)

(58) Field of Classification Search
CPC .................................................. G01N 21/6486
See application file for complete search history.

(56) References Cited

U.S. PATENT DOCUMENTS

2013/0162999 A1* 6/2013 Myrick ..................... G01J 3/28
356/402
2020/0278300 A1* 9/2020 Dunker ................ G06V 20/693

FOREIGN PATENT DOCUMENTS

JP         2019-165687         10/2019

OTHER PUBLICATIONS

Shimasaki, Yohei et al., "Comparative Analysis of Excitation Fluorescence Spectra in Several Phytoplankton Cultivated Strains", Program and Abstracts of Japanese Society of Fisheries Science Meeting in Spring in 2014. Japanese Society of Fisheries Science Meeting in Spring in 2014, Mar. 27, 2014, p. 143.

(Continued)

*Primary Examiner* — Hugh Maupin
(74) *Attorney, Agent, or Firm* — Wenderoth, Lind & Ponack, L.L.P.

(57) ABSTRACT

An abundance of specific species of phytoplankton in a phytoplankton group in which a plurality of kinds coexists is calculated in a simple manner. Based on a reference sample intensity ratio $r_0$, a reference sample total fluorescence intensity $I_0$, and an existing quantity $K_0$ of specific species of phytoplankton, an intensity ratio $r_d$ of other species of plankton is calculated. An analysis sample that is expected to have similarity with the reference sample is irradiated with the excitation light, an intensity of fluorescence emitted from the analysis sample is measured in each of wavelength bands A and B, and an intensity ratio r is calculated. A total fluorescence intensity I is measured, and an existing quantity K of the specific species of the phytoplankton is calculated based on the intensity ratio $r_d$ of other (Continued)

species of plankton, the intensity ratio r, and the total fluorescence intensity I.

9 Claims, 6 Drawing Sheets

(56) References Cited

OTHER PUBLICATIONS

Shimasaki, Yohei et al., "Study on Monitoring Method of Red Tide Dynamics of Dinoflagellate Karenia Mikimotoi Using Excitation Fluorescence Spectrum", Program and Abstracts of Japanese Society of Fisheries Science Meeting in Spring in 2016. Japanese Society of Fisheries Science Meeting in Spring in 2016, Mar. 26, 2016, p. 86.
Shimasaki, Yohei et al., "Study on Field Monitoring of Harmful Dinoflagellate Karenia Mikimotoi Using Underwater Observation Type Fluorescence Spectrometer", Program and Abstracts of Japanese Society of Fisheries Science Meeting in Spring in 2017. Japanese Society of Fisheries Science Meeting in Spring in 2017, Mar. 26, 2017, p. 81.
Saito, Toshiyuki et al., "A Method of in situ Measurement for Counting and Sizing of Blue-Green Alga Particles by the Detection of Fluorescent Components at Two Wavelengths", The Review of Laser Engineering vol. 24, No. 4, published by The Laser Society of Japan, Apr. 1996, pp. 499-506.
International Preliminary Report on Patentability dated Sep. 28, 2021 in International (PCT) Application No. PCT/JP2020/006889.

* cited by examiner

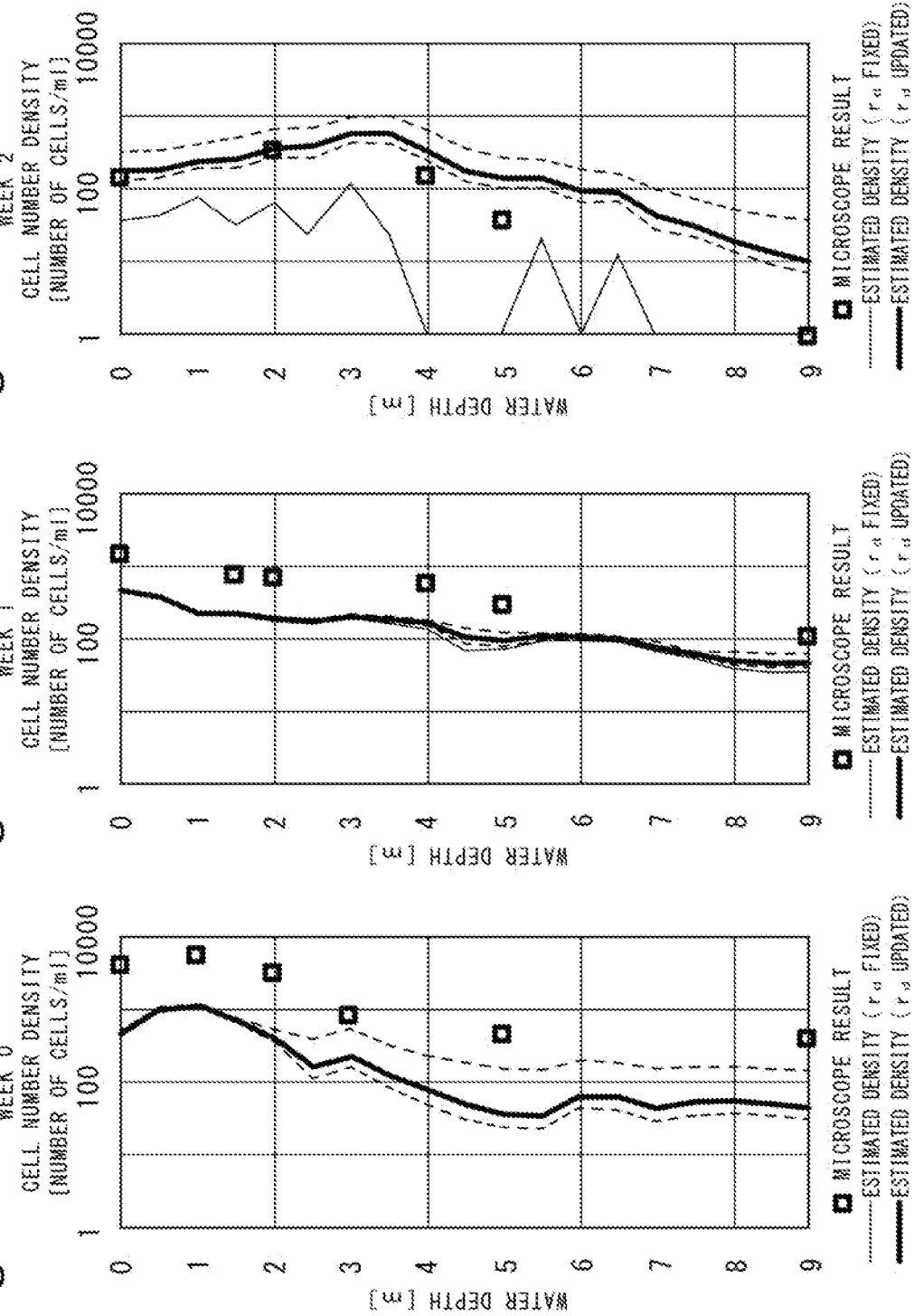

METHOD AND APPARATUS FOR CALCULATING ABUNDANCE OF SPECIFIC SPECIES OF PHYTOPLANKTON, AND METHOD AND APPARATUS FOR DETECTING SIGN OF RED TIDE OCCURRENCE CAUSED BY SPECIFIC SPECIES OF PHYTOPLANKTON

TECHNICAL FIELD

The present invention relates to a method and an apparatus for calculating an abundance of specific species of phytoplankton, and a method and an apparatus for detecting sign of red tide occurrence caused by specific species of phytoplankton.

BACKGROUND ART

When specific species of phytoplankton such as *Karenia mikimotoi* and/or *Chattonella antiqua* proliferates, a so-called red tide occurs, and the phytoplankton may be mixed into a cage in an aqua culture. When the phytoplankton of this kind proliferates, the fishery industry may be damaged significantly by mass mortality of cultivated fish. For this reason, conventionally, various efforts have been made to detect a sign of red tide occurrence.

For example, it is known that by observing a sample collected on site with a microscope, the number of phytoplankton contained in the sample is counted while kinds of the phytoplankton contained in the sample are identified and thereby an abundance thereof is measured.

Further, as another method, it is known that an abundance of phytoplankton is measured in a simple manner by measuring the intensity of fluorescence emitted from a fluorescent pigment (for example, chlorophyll) of the phytoplankton when irradiated with excitation light using an optical chlorophyll meter (for example, Infinity-CLW manufactured by JFE Advantech Co., Ltd.).

Further, as another method, it is known to roughly classify kinds of phytoplankton on the "class" level by measuring an intensity pattern (excitation spectrum) of fluorescence emitted from a fluorescent pigment of the phytoplankton when irradiated with excitation light in a plurality of excitation wavelengths using a multi-wavelength excitation fluorometer (for example, Multi-Exciter manufactured by JFE Advantech Co., Ltd.).

As another method, it is known to detect *Karenia mikimotoi* as specific species of phytoplankton by gene analysis. For example, it is known that, by using "Red Tide Causative Plankton Detection Kit 1-*Karenia mikimotoi*" sold by NIPPON GENE CO., LTD., whether or not *Karenia mikimotoi* is present in a sample collected on site is analyzed on the "species" level by checking a difference in genes by a LAMP method.

Further, as another method, Non-Patent Documents 1 to 3 disclose that a peak wavelength of a fluorescence spectrum of specific species of phytoplankton (for example, *Karenia mikimotoi* and *Chattonella antiqua*) is located on the longer wavelength side than other algae on a fluorescence spectrum of phytoplankton when irradiated with excitation light of around 435 nm. Furthermore, a ratio (f685/670) of the fluorescence intensity at a wavelength of 685 nm to the fluorescence intensity at a wavelength of 670 nm in the fluorescence spectrum of the specific species of the phytoplankton described above is higher than that of other algae, which suggests the possibility of monitoring an abundance of the specific species of the phytoplankton based on the ratio (f685/670) of the fluorescence intensity.

Further, as another method, Non-Patent Document 4 suggests that the fluorescence intensity at each of a wavelength of 655 nm and a wavelength of 685 nm is measured when each phytoplankton in a sample is irradiated with excitation light, and the phytoplankton are extremely roughly classified on the "phylum" level in such a manner that blue-green algae is identified in a case where the fluorescence intensity at the wavelength of 655 nm is larger, and other phytoplankton are identified in a case where the fluorescence intensity at the wavelength of 685 nm is larger.

PRIOR ART DOCUMENT

Non-Patent Document

Non-Patent Document 1: Yohei SHIMASAKI, (and seven others), "Comparative Analysis of Excitation Fluorescence Spectra in Several Phytoplankton Cultivated Strains", Program and Abstracts of Japanese Society of Fisheries Science Meeting in Spring in 2014. Japanese Society of Fisheries Science Meeting in Spring in 2014, issued on Mar. 27, 2014, p. 143.

Non-Patent Document 2: Yohei SHIMASAKI, (and six others), "Study On Monitoring Method of Red Tide Dynamics of Dinoflagellate *Karenia Mikimotoi* Using Excitation Fluorescence Spectrum", Program and Abstracts of Japanese Society of Fisheries Science Meeting in Spring in 2016. Japanese Society of Fisheries Science Meeting in Spring in 2016, issued on Mar. 26, 2016, p. 86.

Non-Patent Document 3: Yohei SHIMASAKI, (and seven others), "Study on Field Monitoring of Harmful Dinoflagellate *Karenia Mikimotoi* Using Underwater Observation Type Fluorescence Spectrometer", Program and Abstracts of Japanese Society of Fisheries Science Meeting in Spring in 2017. Japanese Society of Fisheries Science Meeting in Spring in 2017, issued on Mar. 26, 2017, p. 81.

Non-Patent Document 4: Toshiyuki SAITO, (and two others), "A Method of in Situ Measurement for Counting and Sizing of Blue-Green Alga Particles by the Detection of Fluorescent Components at Two Wavelengths", The Review of Laser Engineering Vol. 24, No. 4, published by The Laser Society of Japan, April 1996, p. 499-506.

SUMMARY OF THE INVENTION

Problems to be Solved by the Invention

In the case of observation with a microscope, it takes a lot of time and effort to collect water, identify species, and count the number of species, so that frequency and location for measurement are limited.

In the case of use of the optical chlorophyll meter, only information on a total amount of phytoplankton can be obtained, and thus an abundance of specific species of phytoplankton cannot be known.

In the case of use of the multi-wavelength excitation fluorometer and the method of Non-Patent Document 4, only classification on a coarse level of phytoplankton is performed, and it is not possible to perform classification on a "species" level necessary for discriminating specific species of phytoplankton (for example, *Karenia mikimotoi* and *Chattonella antiqua*) that may be a factor of red tide occurrence.

According to gene analysis, it is possible to classify phytoplankton on "species" level, and thus it is possible to know whether or not specific species of phytoplankton is present. However, it is not possible to know an abundance thereof since the number of genes is not controlled and is amplified at a high magnification. In addition, there are a point that it is necessary to prepare a syringe, a heating and moisturizing tool, etc., and carefully use them, a point that it is necessary to control a temperature of a reagent at a low temperature and it takes time and effort to handle the reagent, and a point that automatic measurement and determination are not possible since a person needs to be involved in work and determination, and there also is a practical restriction.

According to Non-Patent Documents 1 to 3, a mechanism of a phenomenon in which a peak of a fluorescence spectrum of specific species of phytoplankton shifts (hereinafter, this phenomenon may be referred to as a spectral shift) is not presented, and it has not been known under what condition measurement is performed, and what calculation is performed using what parameter to obtain useful information.

That is, in the conventional method, it is not possible to obtain, in a simple manner, an abundance of specific species of phytoplankton in phytoplankton group in which a plurality of kinds coexists. This becomes a great restriction on detection of a sign of red tide that is not known to occur when or where.

An object of the present invention is to provide a method and an apparatus for calculating an abundance of specific species of phytoplankton, and a method and an apparatus for detecting sign of red tide occurrence caused by specific species of phytoplankton, each of which can calculate, in a simple manner, an abundance of specific species of phytoplankton in a phytoplankton group in which a plurality of kinds coexist.

Means for Solving the Problems

The inventor of the present application has obtained knowledge described below on a mechanism of the phenomenon of the peak shift observed in a fluorescence spectrum of specific species of phytoplankton. That is, a fluorescent pigment contained in phytoplankton absorbs excitation light and emits fluorescence. A part of the fluorescence is resorbed by the fluorescent pigment and fluorescence is reemitted by the fluorescent pigment.

This resorption is likely to occur in fluorescence having a wavelength in which an absorption is occurred more largely, and is less likely to occur in fluorescence having a wavelength in which an absorption is occurred little. For example, in the vicinity of a longer wavelength side limit (referred to as an absorption end) of an absorption spectrum (a wavelength region in which absorption decreases as the wavelength increases), absorption is likely to occur when a wavelength becomes shorter within the range, and fluorescence that is not absorbed by an individual phytoplankton but is transmitted and detected becomes weak accordingly. In contrast, as the wavelength becomes longer and approaches the absorption end, absorption is less likely to occur, and the fluorescence detected outside an individual phytoplankton is less likely to become weak. When considering the vicinity of the peak of the fluorescence spectrum, the likelihood of absorption of fluorescence decreases as the wavelength becomes longer. Accordingly, the shorter wavelength causes fluorescence to be weakened by resorption as compared with the longer wavelength, and thus the peak of the fluorescence spectrum shifts to the longer wavelength side.

The likelihood of resorption depends on how many fluorescent pigments are there in the proximity to a fluorescent pigment where fluorescence is emitted first. In *Karenia mikimotoi* and the *Chattonella antiqua* as specific species of phytoplankton, when checked with a microscope, fluorescent pigments (chloroplasts) are close to each other and spatially dense, and thus resorption easily occurs as compared with other phytoplankton. The present invention is based on the above knowledge.

One aspect of the present invention provides a method of calculating an abundance of specific species of phytoplankton, the calculation method including:

irradiating a reference sample containing a phytoplankton group with excitation light, the phytoplankton group containing a plurality of kinds of phytoplankton, the plurality of kinds of phytoplankton possibly including the specific species of the phytoplankton, and the specific species of the phytoplankton emitting fluorescence by absorbing the excitation light;

measuring an intensity of the fluorescence emitted from the reference sample in each of two wavelength bands and calculating a reference sample intensity ratio that is a ratio of intensities of these two;

measuring a reference sample total fluorescence intensity that is an intensity in a substantially entire wavelength band of the fluorescence emitted from the reference sample;

counting a reference abundance of the specific species of the phytoplankton contained in the reference sample;

calculating an other species plankton intensity ratio, that is a ratio of intensities in the two wavelength bands of the fluorescence emitted from other species of phytoplankton other than the specific species of the phytoplankton in the phytoplankton group, based on the reference sample intensity ratio, the reference sample total fluorescence intensity, and the reference abundance;

irradiating an analysis sample, which is expected to have similarity with the reference sample with respect to composition of the phytoplankton group, with excitation light;

measuring an intensity of the fluorescence emitted from the analysis sample in each of the two wavelength bands and calculating an intensity ratio that is a ratio of intensities of these two;

measuring a total fluorescence intensity that is an intensity in a substantially entire wavelength band of the fluorescence emitted from the analysis sample; and calculating an abundance of the specific species of the phytoplankton that may be contained in the analysis sample based on the other species plankton intensity ratio, the intensity ratio, and the total fluorescence intensity.

Here, in the present specification, the abundance includes a quantitative existing quantity, as well as a qualitative index or expression.

Further, the substantially entire wavelength band means a wavelength range in which measurement can be performed in a wide range sufficient for estimating a fluorescence intensity in the entire wavelength band without measuring the entire wavelength band.

Further, the analysis sample that is expected to have similarity with the reference sample includes not only a case where a location, or a location and time of the analysis sample are the same as or sufficiently close to those of the reference sample, but also a case where the composition of the phytoplankton group is expected to be sufficiently close even if a location, or a location and time of the reference sample are far away. In other words, between the reference sample and the analysis sample, in general, the closer locations or locations and time are, the more similar the composition of the phytoplankton group is expected. However, even if the reference sample and the analysis sample are physically and temporally away from each other, there is a case where similarity in the composition of the phytoplankton group is expected, and this case also means inclusion in the analysis sample.

According to the present invention, it is possible to calculate (estimate) an abundance of the specific species of the phytoplankton having relatively large resorption, for example, on the basis of the intensity of fluorescence measured in a plurality of wavelength bands having different degrees of likelihood of occurrence of resorption. Furthermore, by measuring the intensity of fluorescence in a wavelength band having a range rather than a pinpoint wavelength band, measurement variation and measurement noise are reduced, so that a highly robust measurement result can be easily obtained.

For calculating the abundance of the specific species of the phytoplankton based on the intensity of fluorescence measured in the two wavelength bands, a method below can be considered. First, for each of the specific species of the phytoplankton and other species of the phytoplankton that may exist in the analysis sample, the intensity of fluorescence emitted per unit abundance in each of the two wavelength bands is measured in advance. Next, the intensity of fluorescence emitted from the sample to be analyzed is measured in each of the two wavelength bands.

Then, for each of the two wavelength bands, two equations in which the measured intensity of fluorescence is represented as the sum of the intensity of fluorescence emitted from the specific species of the phytoplankton and the intensity of fluorescence emitted from other species of the phytoplankton are established. Here, the intensity of the fluorescence emitted from the specific species of the phytoplankton of and other species of the phytoplankton is expressed by multiplying an abundance of each by the intensity of fluorescence emitted per unit abundance of each. Finally, by solving these two equations, the abundance of the specific species of the phytoplankton is calculated.

In the above method, it is assumed that which species of phytoplankton is contained in the analysis sample is clear, and it is necessary to measure in advance the intensity of fluorescence per unit abundance for each phytoplankton contained in the analysis sample.

Here, for the specific species of the phytoplankton to be analyzed, a sample containing a single species of the specific species of the phytoplankton can be prepared, and the intensity of fluorescence emitted per unit abundance can be measured in advance.

However, phytoplankton contained in the analysis sample may vary depending on a location to be analyzed. For this reason, since it is not known in advance what species of phytoplankton is contained in the analysis sample, it is not possible to prepare in advance a sample containing only other species of the phytoplankton, and it is not possible to measure in advance the intensity of fluorescence emitted from other species of the phytoplankton per unit abundance. In addition, there is a case where a plurality of kinds of other species of phytoplankton exist, and it is not easy to measure the intensity of fluorescence emitted per unit abundance for each of the phytoplankton.

In this regard, in the present invention, the other species plankton intensity ratio is calculated in advance based on the reference sample, and it is not necessary to measure in advance the intensity of fluorescence emitted from other species of the phytoplankton per unit abundance. Further, the other species plankton intensity ratio is calculated as other species of the entire phytoplankton excluding the specific species of the phytoplankton in the phytoplankton group regardless of whether the number of species of other species of the phytoplankton is one or more. Furthermore, since the analysis sample is expected to have similarity with the reference sample with respect to the composition of the phytoplankton group, the abundance of the specific species of the phytoplankton in the analysis sample can be calculated by diverting the other species plankton intensity ratio based on the reference sample.

Therefore, the abundance of the specific species of the phytoplankton can be calculated without the need to grasp other species of phytoplankton included in the analysis sample in advance.

Preferably, the abundance is the existing quantity of the specific species of the phytoplankton.

Here, in the present specification, the existing quantity has a comprehensive meaning including the number of cells and a ratio. For example, the abundance of the specific species of the phytoplankton means any of the number of cells, the density (number of cells/ml), and an abundance ratio of the specific species of the phytoplankton to other phytoplankton, and the number of cells of the specific species of the phytoplankton with respect to the number of cells of the entire phytoplankton group.

According to the present configuration, the abundance of the specific species of the phytoplankton can be grasped as an absolute value.

Preferably, the abundance is expressed as an index based on the existing quantity of the specific species of the phytoplankton.

According to the present configuration, it is easy to grasp the abundance of the specific species of the phytoplankton.

Preferably, the index is represented by an expression indicating the degree of the existing quantity.

According to the present configuration, it is easy to grasp the degree of the existing quantity of the specific species of the phytoplankton by an index represented by an expression indicating the degree.

Preferably, the other species plankton intensity ratio is calculated based on a plurality of sets of the reference sample intensity ratio, the reference sample total fluorescence intensity, and the reference abundance, which are measured or calculated for each of a plurality of the reference samples.

According to the present configuration, variation of the reference sample is reduced based on a plurality of sets of the reference sample intensity ratio, the reference sample total fluorescence intensity, and the reference abundance, and the reliability of the other species plankton intensity ratio is improved.

Preferably, the other species plankton intensity ratio is updated over time.

According to the present configuration, the other species plankton intensity ratio is updated as appropriate in accordance with a temporal change in the phytoplankton group that may exist in the sampling target location, so that the reliability of the abundance of the specific species of the phytoplankton is improved.

Further, another aspect of the present invention provides a sign detection method for red tide occurrence caused by specific species of phytoplankton, the specific species of the phytoplankton being possibly a cause of red tide occurrence, the sign detection method including:

detecting a sign of red tide occurrence based on the abundance calculated by the method for calculating the abundance of the specific species of the phytoplankton according to any one of the above.

According to the present invention, a sign of red tide occurrence can be detected on the basis of an estimated abundance of the specific species of the phytoplankton.

Still another aspect of the present invention provides an apparatus for calculating an abundance of specific species of phytoplankton, the apparatus including:

an excitation light generation unit that irradiates a reference sample containing a phytoplankton group with excitation light, the phytoplankton group containing a plurality of kinds of phytoplankton, the plurality of kinds of phytoplankton possibly including the specific species of the phytoplankton, and the specific species of the phytoplankton emitting fluorescence by absorbing the excitation light;

a fluorescence intensity measurement unit that measures a reference sample wavelength band fluorescence intensity that is an intensity in each of two wavelength bands and a reference sample total fluorescence intensity that is an intensity in a substantially entire wavelength band; and a calculation unit that calculates a reference sample intensity ratio that is a ratio of the two reference sample wavelength band fluorescence intensities and calculates an other species plankton intensity ratio that is a ratio of intensities in each of the two wavelength bands of the fluorescence emitted from other species of phytoplankton other than the specific species of the phytoplankton in the phytoplankton group based on the reference sample intensity ratio, the reference sample total fluorescence intensity, and a reference abundance counted in advance in the specific species of the phytoplankton contained in the reference sample, wherein the excitation light generation unit irradiates an analysis sample, which is expected to have similarity with the reference sample with respect to composition of the phytoplankton group, with excitation light, the fluorescence intensity measurement unit measures a wavelength band fluorescence intensity that is an intensity in each of the two wavelength bands of the fluorescence emitted from the analysis sample and a total fluorescence intensity that is an intensity in a substantially entire wavelength band of the fluorescence emitted from the analysis sample, and the calculation unit calculates an intensity ratio that is a ratio of two of the wavelength band fluorescence intensities, and calculates an abundance of the specific species of the phytoplankton that may be contained in the analysis sample based on the other species plankton intensity ratio, the intensity ratio, and the total fluorescence intensity.

Further, further another aspect of the present invention provides a sign detection apparatus for red tide occurrence caused by specific species of phytoplankton, the sign detection apparatus including a sign detection unit that detects a sign of red tide occurrence caused by the specific species of the phytoplankton based on the abundance of the specific species of the phytoplankton calculated by the apparatus for calculating an abundance of the specific species of the phytoplankton.

Effect of the Invention

According to the present invention, it is possible to calculate, in a simple manner, the abundance of the specific species of the phytoplankton even in a phytoplankton group in which a plurality of kinds coexists.

BRIEF DESCRIPTION OF THE DRAWINGS

FIGS. 10A, 10B, and 10C are graphs showing a relationship between a calculation result of an abundance of specific species of phytoplankton and the abundance observed with a microscope.

MODE FOR CARRYING OUT THE INVENTION

Hereinafter, an embodiment according to the present invention will be described with reference to the accompanying drawings. Note that description below is merely exemplary in nature and is not intended to limit the present invention, its application, or its use. Further, the drawings are schematic, and ratios of dimensions and the like are different from actual ones.

Figure 1:
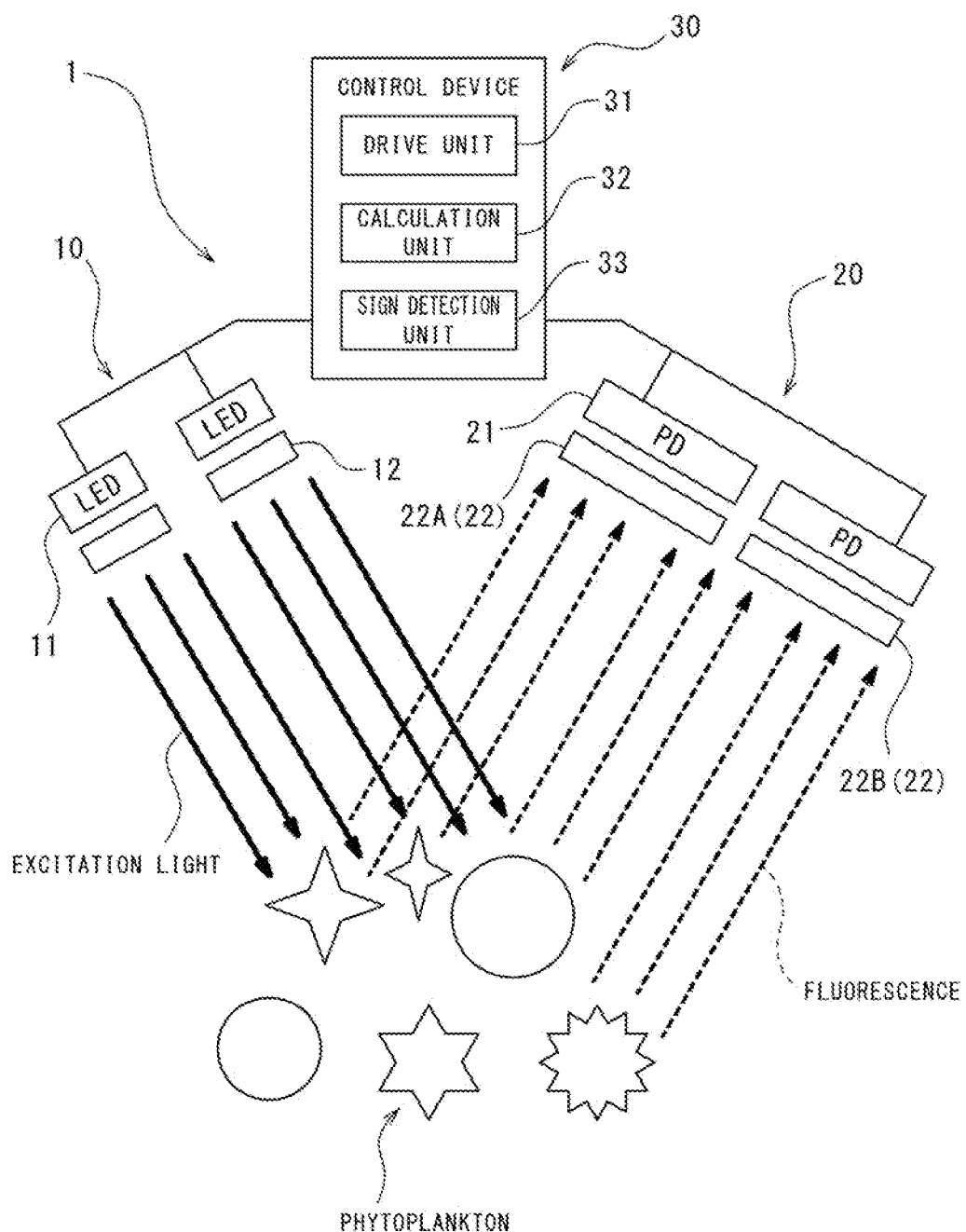
FIG. 1 is a diagram illustrating a schematic configuration of an apparatus for calculating an abundance of specific species of phytoplankton according to a first embodiment of the present invention.

FIG. 1 illustrates a schematic configuration of the calculation apparatus 1 for calculating an abundance of specific species of phytoplankton according to an embodiment of the present invention. As illustrated in FIG. 1, the calculation apparatus 1 includes an excitation light generation unit 10 that irradiates a sample to be measured containing phytoplankton with excitation light, a fluorescence intensity measurement unit 20 that measures fluorescence emitted from the sample by the excitation light, and a control device 30 that controls drive of these units and analyzes a measurement result.

The excitation light generation unit 10 includes a light emitting element 11 and a light sending optical filter unit 12. The light emitting element 11 has a light sending axis toward the sample, and is configured to emit excitation light of a predetermined intensity toward the sample. In the present embodiment, a light emitting diode (LED) is employed as the light emitting element 11.

The light sending optical filter unit 12 is arranged between the light emitting element 11 and the sample to be measured in a manner facing the light sending axis of the light emitting element 11, and is configured to allow excitation light in a specific wavelength band in the excitation light emitted by the light emitting element 11 to pass through and cut excitation light of other wavelengths. In the present embodiment, the light sending optical filter unit 12 includes, for example, a thin film filter or a glass filter.

Note that, in the present embodiment, a wavelength band by the light sending optical filter unit 12 is set so that chlorophyll a, which is one of fluorescent pigments contained in phytoplankton, can be efficiently excited. Specifically, referring to FIG. 2 (FIG. 4.2, disclosed in Sven Beer, Mats Bjork ("o" with an umlaut symbol), and John Beardall, "Photosynthesis in the Marine Environment, First Edition") showing absorption spectra of the chlorophyll a and chlorophyll b, the chlorophyll a has large absorption in a wavelength band of a wavelength of about 420 nm to about 450 nm. In the present embodiment, in order that the chlorophyll a is efficiently excited, excitation light in a wavelength band in which a center wavelength at which absorption into the chlorophyll a is large is 435 nm and a half peak width is about 120 nm is used as the excitation light.

The fluorescence intensity measurement unit 20 includes a light receiving element 21 and a light receiving optical filter unit 22. The light receiving element 21 is arranged to face the sample, and is configured to measure fluorescence emitted from the sample by the excitation light. In the present embodiment, a photodiode PD is employed as the light receiving element 21.

The light receiving optical filter unit 22 is arranged between the light receiving element 21 and the sample to be measured so as to face a light receiving axis of the light receiving element 21, and is configured to allow fluorescence in a specific wavelength band of fluorescence emitted from the sample to pass through and cut the other. In the present embodiment, two types, light receiving optical filter units 22A and 22B, corresponding to different wavelength bands A and B are provided.

The wavelength band A has a center wavelength of 670 nm and a half peak width of 12 nm. The wavelength band B has a center wavelength of 690 nm and a half peak width of 12 nm. That is, the light receiving optical filter unit 22A allows fluorescence having a wavelength of approximately 664 nm or more and 676 nm or less to pass through, and cuts other wavelength components. The light receiving optical filter unit 22B allows fluorescence having a wavelength of approximately 684 nm or more and 696 nm or less to pass through, and cuts other wavelength components. Note that, although not illustrated, in the calculation apparatus 1, the light receiving element 21 can also measure the intensity of fluorescence emitted from the sample in the entire wavelength band without the light receiving optical filter unit 22.

The control device 30 is composed of a well-known computer including a CPU, a memory, a storage device, and an input/output device, and software implemented in the computer. The control device 30 includes a drive unit 31, a calculation unit 32, and a sign detection unit 33.

The drive unit 31 controls emission of excitation light from the light emitting element 11 by supplying power to the light emitting element 11 of the excitation light generation unit 10. The calculation unit 32 mathematically analyzes the intensity of fluorescence measured by the light receiving element 21 of the fluorescence intensity measurement unit 20, and calculates and estimates an abundance of specific species of phytoplankton contained in the sample. The sign detection unit 33 detects a sign of red tide occurrence on the basis of the abundance of specific species of phytoplankton calculated by the calculation unit 32.

Hereinafter, a calculation algorithm for calculating an abundance of specific species of phytoplankton in the calculation unit 32 and sign detection of red tide occurrence due to the sign detection unit 33 will be described.

The inventor of the present application has paid attention to, as specific species of phytoplankton, harmful species of phytoplankton that may cause red tide occurrence, more specifically, specific harmful species of phytoplankton such as *Karenia mikimotoi* and *Chattonella antiqua* (hereinafter referred to as the specific species of the phytoplankton), and has found a phenomenon in which a peak of a fluorescence spectrum of these is shifted (hereinafter, referred to as the peak shift) to the longer wavelength side as compared to a fluorescence spectrum of other species of phytoplankton (mainly harmless species of phytoplankton that hardly cause red tide, including harmful species of phytoplankton other than *Karenia mikimotoi* and *Chattonella antiqua*, and, hereinafter, collectively referred to as harmless species of phytoplankton or other species of phytoplankton for simplicity of the description). The inventor of the present application has found a method for calculating an abundance of the specific species of the phytoplankton of using this phenomenon by clarifying the mechanism of this phenomenon.

Figure 3:
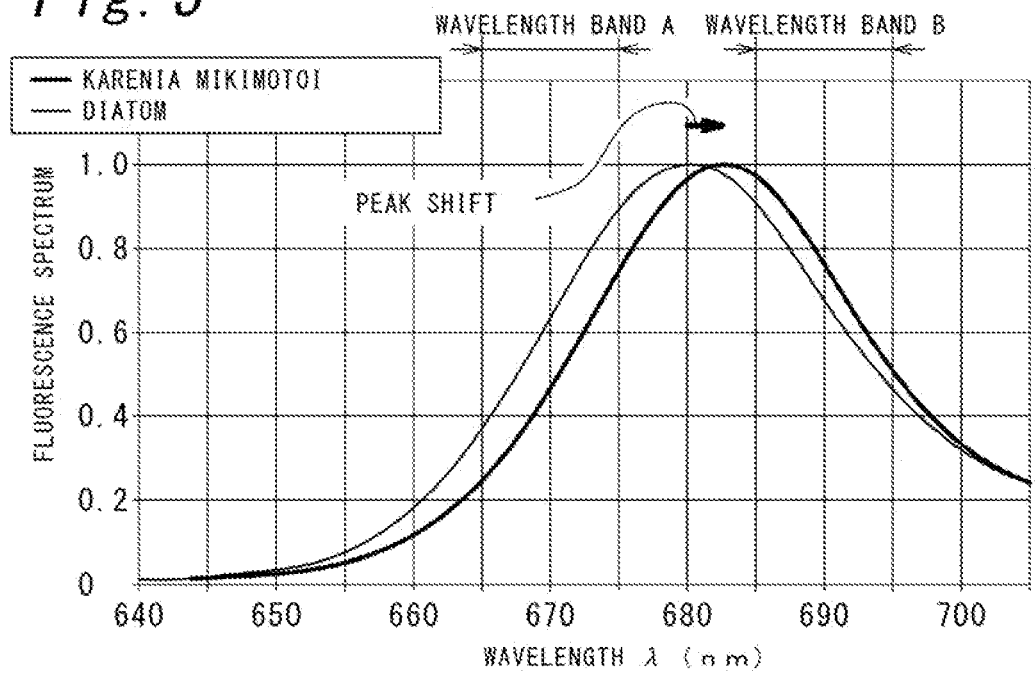
FIG. 3 is a graph showing a fluorescence spectrum of phytoplankton.

FIG. 3 illustrates fluorescence spectra when two kinds of phytoplankton are irradiated with excitation light. Here, the fluorescence spectrum in the present embodiment means a normalized spectrum normalized by dividing, by a maximum intensity value in a measured wavelength band, all the other intensity values.

In FIG. 3, a fluorescence spectrum of *Karenia mikimotoi* is indicated by a thick line as an example of the specific species of the phytoplankton, and a fluorescence spectrum of a diatom is indicated by a thin line as an example of other species of phytoplankton. Further, a detector (for example, a spectroscope) having high resolution measures the intensity of fluorescence that is obtained when a sample containing a single species of phytoplankton is irradiated with excitation light, and thus each fluorescence spectrum is obtained.

As shown in FIG. 3, the fluorescence spectrum of a diatom has a peak at about 681 nm, whereas the fluorescence spectrum of *Karenia mikimotoi* has a peak at about 683 nm. That is, in *Karenia mikimotoi*, the peak of the fluorescence spectrum is located on the longer wavelength side by about 2 nm than that of the diatom. As a result of intensive studies, the inventor of the present application has found that this shift peak is caused by resorption of fluorescence by a fluorescent pigment (chlorophyll a) of the phytoplankton.

Figure 2:
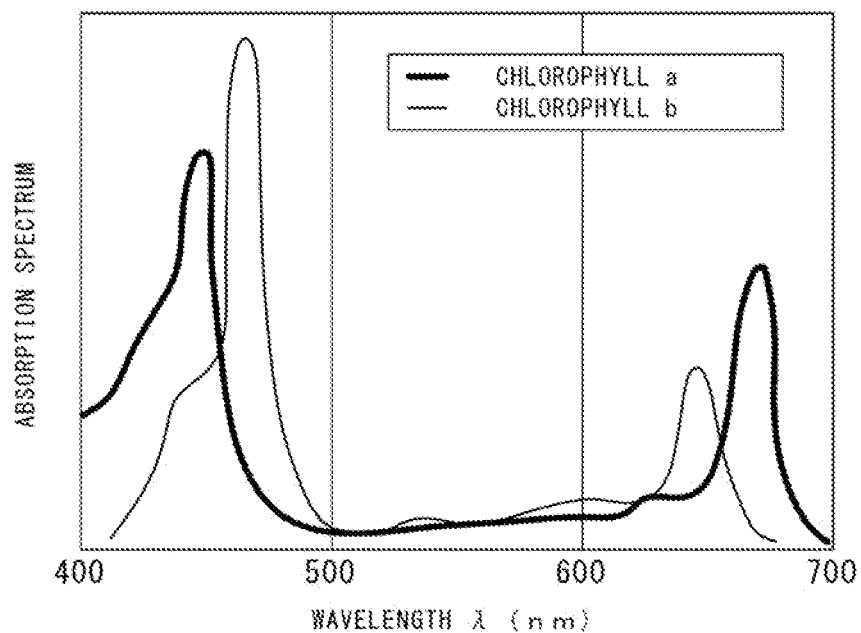
FIG. 2 is a graph showing absorption spectra of chlorophyll a and chlorophyll b.

Referring also to FIG. 2, a peak of an absorption spectrum of the chlorophyll a also exists around 670 nm. In the vicinity of a longer wavelength side limit (referred to as an absorption end) of this peak (a wavelength region in which absorption decreases as the wavelength increases), absorption is more likely to occurs as the wavelength decreases, whereas absorption is less likely to occur as the wavelength increases and approaches the absorption end. That is, in the wavelength band around about 670 nm where the peak is located, absorption by the chlorophyll a is likely to occur, whereas absorption by the chlorophyll a is unlikely to occur at the absorption end around about 690 nm.

That is, of fluorescence emitted by excitation light, fluorescence in a wavelength band around about 670 nm is likely to be resorbed by the other chlorophyll a within the same individual, while fluorescence in a wavelength band around about 690 nm is less likely to be resorbed by the other chlorophyll a and is emitted to the outside. Likelihood of this resorption depends on how much chlorophyll a is in the proximity to the chlorophyll a in which fluorescence is emitted first. The specific species of the phytoplankton such as *Karenia mikimotoi* and *Chattonella antiqua* contain a large amount in volume of the chlorophyll a in the proximity to each other, and thus it is considered that resorption is likely to occur as compared with other species of phytoplankton.

Figure 4A:
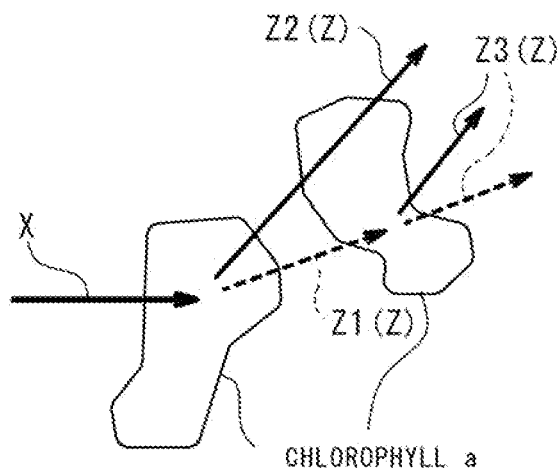
FIGS. 4A and 4B are diagrams explaining a mechanism in which a peak shift of a fluorescence spectrum occurs in specific species of phytoplankton.
Figure 4B:
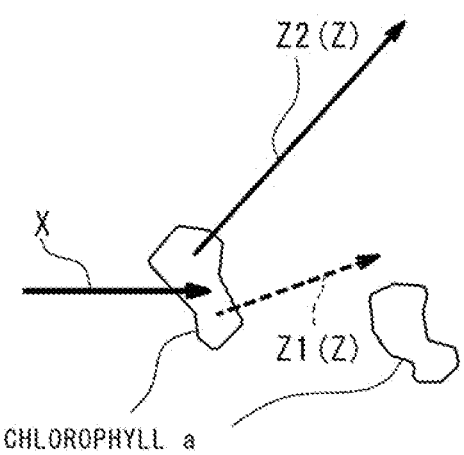

FIGS. 4A and 4B conceptually illustrate fluorescence emitted by excitation light, FIG. 4(*a*) illustrates a case of the specific species of the phytoplankton, and FIG. 4(*b*) illustrates a case of other species of phytoplankton. Referring to FIG. 4(*a*), the chlorophyll a as a fluorescent pigment contained in the specific species of the phytoplankton absorbs excitation light X having a short wavelength of 435 nm as a center wavelength, and emits fluorescence Z having a wavelength longer than that of the excitation light X. The fluorescence Z includes fluorescence Z1 having a wavelength of about 670 nm and a relatively short wavelength and fluorescence Z2 having a wavelength of about 690 nm and a relatively long wavelength.

As illustrated in FIG. 4(*a*), the fluorescence Z2 is less likely to be resorbed by the chlorophyll a within the same individual, whereas the fluorescence Z1 is resorbed by the chlorophyll a in the same individual, and the intensity of Z1 decreases accordingly. Note that, as a result of the resorption, fluorescence Z3 is further emitted by a part of the energy. The above is considered to occur because, as described above, since the specific species of the phytoplankton, that is, *Karenia mikimotoi* and *Chattonella antiqua* and the like, contain a large amount in volume of the chlorophyll a within the same individual, excitation light is absorbed by one piece of the chlorophyll a, and fluorescence emitted from the chlorophyll a is likely to be resorbed by the chlorophyll a within the same individual.

In contrast, as illustrated in FIG. 4(*b*), it is considered that other species of the phytoplankton do not contain a large amount in volume of the chlorophyll a unlike the specific species of the phytoplankton, and fluorescence emitted from one piece of chlorophyll hardly passes through the chlorophyll a within the same individual body, and thus is less likely to be resorbed.

That is, in the specific species of the phytoplankton, the intensity of fluorescence is weakened by resorption in the vicinity of 670 nm, and thus, it is considered that the peak shift in which a peak of a fluorescence spectrum measured by an external detector appears to shift to the longer wavelength side occurs.

Using this phenomenon, the inventor of the present application has obtained knowledge below when calculating an abundance of the specific species of the phytoplankton.

First, a fluorescent pigment of interest needs to be one that may cause resorption. A fluorescent pigment that emits fluorescence by excitation light and a fluorescent pigment that resorbs fluorescence do not need to be of the same type. However, in general, the chlorophyll a is suitable as a fluorescent pigment in which a large amount of resorption may sufficiently occur.

Secondly, it is necessary to include, as the excitation light, one having energy capable of generating fluorescence that may cause resorption. Excitation light having such low energy that only fluorescence exceeding a wavelength upper limit of an absorption spectrum is emitted is not appropriate.

Thirdly, degrees of resorption need to be different between kinds of phytoplankton to be distinguished.

As described above as an example, *Karenia mikimotoi* and *Chattonella antiqua* have spatial distribution in which a fluorescent pigment easily resorbs fluorescence as compared with other species.

Fourthly, by using the intensity of fluorescence in a plurality of wavelength bands having different degrees of resorption, two unknown amounts, which are an abundance of a kind of plankton which occurs relatively large resorption and an abundance of a kind of plankton which occurs relatively small resorption, can be calculated on the basis of this mechanism.

That is, in the present embodiment, the excitation light generation unit 10 irradiates a sample in a sampling target location with excitation light of predetermined intensity. Note that the sample in the sampling target location includes both a case where a sample is irradiated with excitation light at the sampling target location and a case where a sample collected from the location is irradiated with excitation light at a location different from the sampling target location. The sample includes a phytoplankton group in which a plurality of kinds of phytoplankton may exist. A plurality of kinds of phytoplankton may include the specific species of the phytoplankton (referred to as the specific species of the phytoplankton) and other species of phytoplankton.

Next, with respect to fluorescence emitted from the sample by excitation light, the fluorescence intensity measurement unit 20 measures a wavelength band A fluorescence intensity I670 and a wavelength band B fluorescence intensity I690, which are intensities in the wavelength bands A and B, respectively, by means of the light receiving element 21 via the light receiving optical filter units 22A and 22B, and measures a total fluorescence intensity I, which is an intensity in the entire wavelength band, by means of the light receiving element 21 without the light receiving optical filter unit 22.

Note that the total fluorescence intensity I is not limited to a specific wavelength band like the wavelength bands A and B, and is to measure the intensity of fluorescence in the entire wavelength band in which a dye to be measured is emitted. Strictly speaking, it is sufficient if measurement can be performed in a wide wavelength range based on which the entire wavelength range can be estimated without measuring the entire wavelength range. That is, it is sufficient if measurement can be performed in almost the entire wavelength band that can be regarded as measurement in the substantially entire wavelength band.

After the above, the calculation unit 32 calculates an intensity ratio r that is a ratio of the wavelength band B fluorescence intensity I690 to the wavelength band A fluorescence intensity I670 (that is, I690/I670). Next, the calculation unit 32 mathematically analyzes the intensity ratio r and the total fluorescence intensity I to calculate an existing quantity of the specific species of the phytoplankton. Note that the existing quantity means a quantitative number, and means the number of cells in the present embodiment. The number of cells means the number of individuals and the number of phytoplankton.

Specifically, when assuming an existing quantity of the specific species of the phytoplankton included in the sample is K and an existing quantity of other species of phytoplankton included in the sample is D, Equation (1) for the total fluorescence intensity I in the entire wavelength band of fluorescence emitted from the sample and Equation (2) for the intensity ratio r are established, and simultaneous equations including these two equations are solved, so that the existing quantity K of the specific species of the phytoplankton and the existing quantity D of other species of phytoplankton are calculated.

[Equation 1]

$$I = K \times Ik + D \times Id \tag{1}$$

Ik: Unit fluorescence intensity for specific species of plankton
Id: Unit fluorescence intensity for other species of plankton

[Equation 2]

$$r = \frac{I690}{I670} \tag{2}$$

The unit fluorescence intensity Ik for specific species of plankton is an intensity in the entire wavelength band of fluorescence emitted from the specific species of the phytoplankton per unit quantity (for example, one cell), which is measured by the fluorescence intensity measurement unit 20 when the specific species of the phytoplankton is irradiated with excitation light of a predetermined intensity from the excitation light generation unit 10. For example, a sample including a single species of the specific species of the phytoplankton is prepared, the total fluorescence intensity I is measured in the calculation apparatus 1, and the existing quantity K of the specific species of the plankton included in the sample is counted by, for example, an optical microscope, and the total fluorescence intensity I is divided by the existing quantity K, so that the unit fluorescence intensity Ik for specific species of plankton is calculated.

The unit fluorescence intensity Id for other species of plankton is an intensity in the entire wavelength band of fluorescence emitted from phytoplankton of other species per unit quantity (for example, one cell), which is measured by the fluorescence intensity measurement unit 20 when phytoplankton of other specifies excluding the specific species of the phytoplankton included in the sample are irradiated with excitation light of a predetermined intensity from the excitation light generation unit 10. For example, a sample including one kind or a plurality of kinds of other species of phytoplankton is prepared, the total fluorescence intensity I is measured in the calculation apparatus 1, and the existing quantity D of other species of the plankton included in the sample is counted by, for example, an optical microscope, and the total fluorescence intensity I is divided by the existing quantity D, so that the unit fluorescence intensity Id for other species plankton is obtained.

In Equation (1), it is assumed that the sample includes at least one of one kind of the specific species of the phytoplankton and one or a plurality of kinds of other species of phytoplankton, and the total fluorescence intensity I in the entire wavelength band is expressed by the sum of the fluorescence intensity emitted from the specific species of the phytoplankton in the entire wavelength band and the fluorescence intensity emitted from other species of the phytoplankton in the entire wavelength band.

The fluorescence intensity emitted from the specific species of the phytoplankton in the entire wavelength band is expressed as a value obtained by multiplying the unit fluorescence intensity Ik for specific species of plankton by the existing quantity K of the specific species of the phytoplankton. Similarly, the fluorescence intensity emitted from other species of the phytoplankton in the entire wavelength band is expressed as a value obtained by multiplying the unit fluorescence intensity Id for other species of plankton by the existing quantity D of other species of the phytoplankton.

In Equation (2), the wavelength band A fluorescence intensity I670 is expressed in Equation (3) below as the sum of the intensity of fluorescence emitted from the specific species of the phytoplankton in the wavelength band A and the intensity of fluorescence emitted from other species of phytoplankton in the wavelength band A. Similarly, in Equation (2), the wavelength band B fluorescence intensity I690 is expressed in Equation (4) below as the sum of the intensity of fluorescence emitted from the specific species of the phytoplankton in the wavelength band B and the intensity of fluorescence emitted from other species of phytoplankton in the wavelength band B.

[Equation 3]

$$I670 = K \times Ik670 + D \times Id670 \tag{3}$$

Ik670: Unit fluorescence intensity in wavelength band A for specific species of plankton
Id670: Unit fluorescence intensity in wavelength band A for other species of plankton

[Equation 4]

$$I690 = K \times Ik690 + D \times Id690 \tag{4}$$

Ik690: Unit fluorescence intensity in wavelength band B for specific species of plankton
Id690: Unit fluorescence intensity in wavelength band B for other species of plankton The unit fluorescence intensity in wavelength band A Ik670 for the specific species of plankton and the unit fluorescence intensity in wavelength band B Ik690 for the specific species of plankton are intensities of fluorescence emitted from the unit quantity of the specific species of the phytoplankton in the wavelength bands A and B, respectively. The unit fluorescence intensity Id670 for the other species of plankton wavelength band A and the unit fluorescence intensity in wavelength band B Id690 for the other species of plankton are intensities of fluorescence emitted from the unit quantity of other species of the phytoplankton in the wavelength bands A and B, respectively.

Similarly to Ik and Id, Ik670, Ik690, Id670, and Id690 are calculated based on the sample for which the existing quantities K and D are counted.

Therefore, in Equation (3), the wavelength band A fluorescence intensity I670 is expressed as the sum of a value obtained by multiplying the existing quantity K of the specific species of the phytoplankton by the unit fluorescence intensity in wavelength band A Ik670 for the specific species of plankton and a value obtained by multiplying the existing quantity D of other species of the phytoplankton by the unit fluorescence intensity Id670 in wavelength band A for the other species of plankton. Similarly, in Equation (4), the wavelength band B fluorescence intensity I690 is expressed as the sum of a value obtained by multiplying the existing quantity K of the specific species of the phytoplankton by the unit fluorescence intensity in wavelength band B Ik690 for the specific species of plankton and a value obtained by multiplying the existing quantity D of other species of the phytoplankton by the unit fluorescence intensity in wavelength band B Id690 for the other species of plankton.

The total fluorescence intensity I in Equation (1) and the intensity ratio r in Equation (2) are measured by the calculation apparatus 1 for each sample. Note that Equations (3) and (4) are substituted into the right side of Equation (2).

By mathematically solving Equations (1) and (2) as simultaneous equations, the existing quantity K of the specific species of the phytoplankton and the existing quantity D of other species of the phytoplankton, which are unknown, are calculated. Hereinafter, a calculation formula of the existing quantity K of the specific species of the phytoplankton is shown in Equation (5), and a calculation formula of the existing quantity D of other species of the phytoplankton is omitted.

[Equation 5]

$$\frac{I}{Ik + \frac{r \times Ik670 - Ik690}{Id690 - r \times Id670} \times Id} = \frac{1}{1 + \frac{r \times \frac{Ik670}{Ik} - \frac{Ik690}{Ik}}{\frac{Id690}{Id} - \frac{r \times Id670}{Id}}} \times \frac{1}{Ik} \quad (5)$$

Equation (6) is obtained by further arranging Equation (5). According to Equation (6), it is possible to calculate the existing quantity K of the specific species of the phytoplankton on the basis of I and r obtained by measuring a sample to be analyzed, Ik, Ik670, and Ik690 related to the specific species of the phytoplankton, and Id, Id670, and Id690 related to other species of the phytoplankton.

Here, it is not known in advance which species of a phytoplankton is contained in the sample to be analyzed. For this reason, it is not easy to prepare in advance Id, Id670, and Id690 related to other species of the phytoplankton included in the sample to be analyzed. In the present invention, by further arranging Equation (5), contrivance as shown in Equations (6) to (9) is made to calculate the existing quantity K of the specific species of the phytoplankton without preparing Id, Id670, and Id690 related to other species of the phytoplankton in advance.

[Equation 6]

$$K = \frac{\frac{Id690 - r \times Id670}{Id}}{\frac{Id690 - r \times Id670}{Id} + \frac{r \times Ik670 - Ik690}{Ik}} \times \frac{1}{Ik} \quad (6)$$

$$= \frac{Ik \times (Id690 - r \times Id670)}{Ik \times (Id690 - r \times Id670) + Id \times (r \times Ik670 - Ik690)} \times \frac{1}{Ik}$$

$$= \frac{Id690 - r \times Id670}{(Id690 - r \times Id670) + \frac{Id}{Ik} \times (r \times Ik670 - Ik690)} \times \frac{1}{Ik}$$

$$= \frac{\frac{Id690}{Id670} - r}{\left(\frac{Id690}{Id670} - r\right) + \frac{Id}{Ik} \times \left(r \times \frac{Ik670}{Id670} - \frac{Ik690}{Id670}\right)} \times \frac{1}{Ik}$$

In Equation (6), Id690/Id670 represents a ratio of the unit fluorescence intensity in wavelength band B Id690 for the other species of plankton to the unit fluorescence intensity in wavelength band A Id670 for the other species of plankton, and when this is arranged as intensity ratio $r_d$ of an other species of plankton, Equation (7) is obtained.

[Equation 7]

$$K = \frac{r_d - r}{r_d - r + \frac{Id}{Ik} \times r \times \frac{Ik670}{Id670} - \frac{Id}{Ik} \times \frac{Ik690}{Id670}} \times \frac{1}{Ik} \quad (7)$$

$$= \frac{r_d - r}{r_d - r + \frac{Id}{Ik} \times r \times \frac{Ik670}{Id670} - \frac{Id}{Ik} \times \frac{Ik690}{Id670} \times \frac{Ik690}{Id670}} \times \frac{1}{Ik}$$

In Equation (7), Ik690/Ik670 represents a ratio of the unit fluorescence intensity in wavelength band B Ik690 for the specific species of plankton to the unit fluorescence intensity in wavelength band A Ik670 for the specific species of plankton, and when this is arranged as an intensity ratio $r_k$ of specific species of plankton, and is further arranged by α expressed in Equation (8) below, Equation (9) is obtained.

[Equation 8]

$$\alpha = \frac{Id}{Ik} \times \frac{Ik670}{Id670} \quad (8)$$

[Equation 9]

$$K = \frac{r_d - r}{r_d - r + r \times \alpha - \alpha \times r_k} \times \frac{I}{Ik} = \frac{r - r_d}{(1 - \alpha) \times r - (r_d - \alpha \times r_k)} \times \frac{I}{Ik} \quad (9)$$

In Equation (9), the unit fluorescence intensity Ik for specific species of plankton and the intensity ratio $r_k$ of specific species of plankton are values determined in advance on the basis of the specific species of the phytoplankton to be measured. The total fluorescence intensity I is obtained by measuring a sample to be measured in the calculation apparatus 1.

The constant number α expressed in Equation (8) is set in advance for each specific species of phytoplankton to be analyzed. A method of setting a will be described. A sample in which one kind of the specific species of the phytoplankton to be analyzed of which the existing quantity K and the intensity ratio $r_k$ of specific species of plankton are known is mixed with one kind of other species of the phytoplankton which exists in a large amount in the sample to be analyzed except for the specific species of the phytoplankton, and of which the existing quantity D and the intensity ratio $r_d$ of other species of plankton are known is prepared.

The intensity ratio $r_k$ of specific species of plankton is calculated by preparing a sample in which only a single species of the specific species of the phytoplankton is cultured and measuring the sample in the calculation apparatus 1. Similarly, the intensity ratio $r_d$ of other species of plankton is calculated by preparing a sample in which only a single species of other species of the phytoplankton is cultured and measuring the sample in the calculation apparatus 1. Further, as described above, the unit fluorescence intensity Ik for specific species of plankton is also calculated in advance.

By substituting the known existing quantity K, the unit fluorescence intensity Ik for specific species of plankton, the intensity ratio r, the intensity ratio $r_k$ of specific species of plankton, and the intensity ratio $r_d$ of other species of plankton into Equation (9), the constant number α satisfying Equation (9) is obtained. Note that the constant number α satisfying Equation (9) may be calculated by the least squares method (for example, the non-linear least squares method) using a plurality of sets of K, Ik, r, $r_k$, and $r_d$ obtained from a plurality of samples resulting from the same sample.

Next, the intensity ratio $r_d$ of other species of plankton will be described. In an actual sample, one or a plurality of species of other species of phytoplankton may exist other than the specific species of the phytoplankton.

In this case, it is not easy to prepare the intensity ratio $r_d$ of other species of plankton for each of one or a plurality of other species of phytoplankton included in the sample. For this reason, in the present embodiment, the intensity ratio $r_d$ of other species of plankton is calculated on the basis of Equation (9) using the constant number $\alpha$.

Specifically, with respect to a reference sample in a location to be analyzed, an existing quantity $K_0$ (reference abundance) of the specific species of the phytoplankton included in the reference sample is counted by, for example, an optical microscope, a total fluorescence intensity $I_0$ (reference sample total fluorescence intensity) and an intensity ratio $r_0$ (reference sample intensity ratio) are calculated for the sample using the calculation apparatus 1, and the existing quantity $K_0$, the total fluorescence intensity $I_0$, the intensity ratio $r_0$, the constant number $\alpha$ calculated above, the unit fluorescence intensity Ik for specific species of plankton, and the intensity ratio $r_k$ of specific species of plankton are substituted into Equation (9), so that the intensity ratio $r_d$ of other species of plankton satisfying Equation (9) is calculated.

Therefore, with respect to an analysis sample analyzed separately from the reference sample in a location to be analyzed, the intensity ratio $r_d$ of other species of plankton calculated based on the reference sample is estimated to be the intensity ratio $r_d$ of other species of plankton included in the analysis sample. Here, the analysis sample is the same in existing location, or location and time as the reference sample. Accordingly, the similarity with the reference sample is expected with respect to the composition of a phytoplankton group. Further, the analysis sample may be used not only in a case where the analysis sample and the reference sample are the same or sufficiently close to each other in location, or location and time, but also in a case where the composition of a phytoplankton group is expected to be sufficiently close even if the analysis sample is far away from the reference sample. In other words, in general, the closer the location and time of the reference sample and the location and time of the analysis sample are, the more similar the composition of the phytoplankton group is expected. However, even if the location and time of the reference sample and the location and time of the analysis sample are physically and temporally away from each other, there is a case where similarity in the composition of the phytoplankton group is expected, and this case also means inclusion in the analysis sample. Note that, in the present specification, the fact that the location of the analysis sample is sufficiently close to the location of the reference sample means that the analysis sample exists within a range of a radius of about 1 km from the reference location where the reference sample is analyzed at a field water area or the location collected from the field water area. Further, the fact that the time of the analysis sample is sufficiently close to the time of the reference sample means that the analysis sample is analyzed at a field water area or collected from the field water area within about one week from the time when the reference sample is analyzed at the field water area or collected from the field water area.

Next, in the calculation apparatus 1, the existing quantity K of the specific species of the phytoplankton is calculated as an estimated value from Equation (9) on the basis of the measured total fluorescence intensity I and intensity ratio r, the known unit fluorescence intensity Ik for specific species of plankton and the intensity ratio $r_k$ of specific species of plankton of the specific species of the phytoplankton to be analyzed, and the constant number $\alpha$ and the intensity ratio $r_d$ of other species of plankton. That is, the existing quantity K of the specific species of the phytoplankton is estimated by the calculation unit 32.

That is, it is possible to calculate the existing quantity K of the specific species of the phytoplankton having relatively large resorption and the existing quantity D of other phytoplankton having relatively small resorption based on the fluorescence intensities measured in the two wavelength bands A and B having different likelihood of occurrence of resorption. Here, by measuring the intensity of fluorescence in the wavelength bands A and B having a range rather than a pinpoint wavelength band, measurement variation and measurement noise are reduced, so that a highly robust measurement result can be easily obtained.

Note that selection of the two wavelength bands may be determined not only on the basis of the difference in the likelihood of occurrence of resorption depending on a kind of a phytoplankton, but also on the basis of the magnitude of a difference in fluorescence spectra between the specific species of the phytoplankton and other species of the phytoplankton.

Further, as another method for calculating an abundance of the specific species of the phytoplankton of based on the intensity of fluorescence measured in the two wavelength bands A and B, a method below can be considered. First, for each of the specific species of the phytoplankton and other species of the phytoplankton that may exist in a sample to be analyzed, the intensity of fluorescence emitted per unit quantity in each of the two wavelength bands A and B is measured in advance. Next, the intensity of fluorescence emitted from the sample to be analyzed is measured in each of the two wavelength bands A and B.

Then, for each of the two wavelength bands, two equations in which the measured intensity of fluorescence is represented as the sum of the intensity of fluorescence emitted from the specific species of the phytoplankton and the intensity of fluorescence emitted from other species of the phytoplankton are established. Here, the intensity of the fluorescence emitted from the specific species of the phytoplankton of and other species of the phytoplankton is expressed by multiplying existing quantity of each by the intensity of fluorescence emitted per unit quantity of each. Finally, by solving these two equations, the existing quantity of the specific species of the phytoplankton is calculated.

However, in the above method, it is assumed that which species of a phytoplankton is contained in the analysis sample is clear, and it is necessary to measure in advance the intensity of fluorescence per unit quantity for each phytoplankton contained in the sample to be analyzed.

Here, for the specific species of the phytoplankton to be analyzed, a sample containing a single species of the specific species of the phytoplankton can be prepared, and the intensity of fluorescence emitted per unit quantity can be measured in advance.

In contrast, other species of phytoplankton contained in the analysis sample may vary depending on a location to be analyzed. For this reason, since it is not known in advance what species of a phytoplankton is contained in the analysis sample, it is not possible to prepare in advance a sample containing only other species of the phytoplankton, and it is not possible to measure in advance the intensity of fluorescence emitted from other species of the phytoplankton per unit quantity. In addition, there is a case where a plurality of kinds of other species of phytoplankton exists, and it is not easy to measure the intensity of fluorescence emitted per unit number for each of the phytoplankton.

In this regard, in the present invention, the intensity ratio $r_d$ of other species of plankton is calculated in advance based on the reference sample, and it is not necessary to measure in advance the intensity of fluorescence emitted from other species of the phytoplankton per unit quantity. Further, the intensity ratio $r_d$ of other species of plankton is calculated as other species of the entire phytoplankton excluding the specific species of the phytoplankton in the phytoplankton group regardless of whether the number of species of other species of the phytoplankton is one or more. Furthermore, since the analysis sample is expected to have similarity with the reference sample with respect to the composition of the phytoplankton group, the existing quantity K of the specific species of the phytoplankton in the analysis sample can be calculated (estimated) by estimating the intensity ratio $r_d$ of other species of plankton based on the reference sample to be approximately equal to the intensity ratio $r_d$ of other species of plankton of the analysis sample.

Therefore, the existing quantity K of the specific species of the phytoplankton can be calculated without the need to grasp other species of phytoplankton included in the analysis sample in advance.

Further, the intensity ratio $r_d$ of other species of plankton may be calculated by the least squares method (for example, the non-linear least squares method) in a manner that a plurality of sets of the existing quantity $K_0$, the total fluorescence intensity $I_0$, and the intensity ratio $r_0$ are satisfied on the basis of Equation (9). In this manner, the reliability of the intensity ratio $r_d$ of other species of plankton is improved.

Further, the intensity ratio $r_d$ of other species of plankton may be appropriately updated over time (for example, periodically every week or the like). For example, periodically, the calculation apparatus 1 may be used to calculate the reference sample total fluorescence intensity $I_0$ and the reference sample intensity ratio $r_0$ on the basis of the reference sample in the place to be analyzed, count the reference abundance $K_0$ of the specific species of the phytoplankton contained in the reference sample, and substitute them into Equation (9) to newly calculate the intensity ratio $r_d$ of other species of plankton, so as to update the intensity ratio $r_d$ of other species of plankton in Equation (9). In this manner, the other species plankton intensity ratio ($r_d$) is updated in accordance with a temporal change in the phytoplankton group that may exist in the sampling target location, so that the reliability of the existing quantity (K) of the specific species of the phytoplankton is improved.

Further, the excitation light generation unit 10 includes the light emitting element 11 and the light sending optical filter unit 12, and the fluorescence intensity measurement unit 20 includes the light receiving element 21 and the light receiving optical filter unit 22. That is, since a spectrometer that is large and tends to be expensive is not necessary, the calculation apparatus 1 can be easily made in a compact and inexpensive manner.

The sign detection unit 33 detects a sign of red tide occurrence on the basis of the calculated existing quantity K of the specific species of the phytoplankton. For example, in a case where attention is paid to *Karenia mikimotoi* as the specific species of the phytoplankton, when the existing quantity K per 1 ml of a sample is calculated to be 50 cells or more, it is considered that there is a high possibility of developing to a red tide level in the future, and the sign detection unit 33 detects a sign of red tide occurrence. Further, in a case where attention is paid to *Chattonella antiqua* as the specific species of the phytoplankton, when the existing quantity K per 1 ml of a sample is 10 cells or more, the sign detection unit 33 detects a sign of red tide occurrence.

That is, it is possible to detect a sign of red tide occurrence on the basis of the existing quantity K of the specific species of the phytoplankton. In addition, for example, a change (for example, a growth rate) in the existing quantity K of the specific species of the phytoplankton may be calculated by periodically calculating the existing quantity K of the specific species of the phytoplankton, and a sign of red tide occurrence may be detected in a case where the change exceeds a certain threshold.

Further, in Equation (9), the abundance (K) may take a negative value depending on a relationship between the intensity ratio r, the intensity ratio $r_k$ of specific species of plankton, and the intensity ratio $r_d$ of other species of plankton. In order to prevent this situation, as shown in Equations (10) and (11), replacing the intensity ratio $r_d$ of other species of plankton with a finite monotonically increasing function g(r) having an upper limit value of $r_k$ and a lower limit value of $r_d$ avoids the existing quantity (K) from being a negative value.

[Equation 10]

$$K = \frac{g(r) - r_d}{(1-\alpha) \times g(r) - (r_d - \alpha \times r_k)} \times \frac{1}{Ik} \quad (10)$$

[Equation 11]

$$g(r) = \max(r_d, \min(r_k, r)) \quad (11)$$

Next, a setting method of the wavelength bands A and B will be described.

First, a single species (for example, *Karenia mikimotoi* which is one of the specific species of the phytoplankton) of species that causes a spectrum shift for which it is desired to calculate the existing quantity in distinction from other species of plankton is irradiated with predetermined excitation light, and a fluorescence spectrum is measured by a detector having high wavelength resolution. Note that the specific species of the phytoplankton has a characteristic that a peak of the fluorescence spectrum shifts to a longer wavelength side than the fluorescence spectrum of other species of phytoplankton. Next, in the measured fluorescence spectrum, all intensity values are divided by a maximum intensity value of the fluorescence spectrum (normalization) to obtain a normalized spectrum (referred to as the spectrum K). The spectrum K is expressed as a function K(λ) of a wavelength λ.

Similarly, a fluorescence spectrum is measured for a single species of other species of phytoplankton, and a normalized spectrum is obtained (referred to as the spectrum D). The spectrum D is expressed as a function D(λ) of the wavelength λ.

Next, as shown in Equation (12), a difference spectrum F(λ) that is a difference between the spectrum D(λ) and the spectrum K(λ) is obtained.

[Equation 12]

$$F(\lambda) = K(\lambda) - D(\lambda) \quad (12)$$

A width w of a wavelength band is determined based on the specification of the fluorescence intensity measurement unit 20, that is, the specification of the light receiving optical filter unit 22. Next, as shown in Equation (13), the difference spectrum F(λ) is integrated with the width w of the wavelength band to obtain G(λ).

[Equation 13]

$$G(\lambda) = \int_{\lambda-\frac{w}{2}}^{\lambda+\frac{w}{2}} F(\lambda) d\lambda \quad (13)$$

Figure 5:
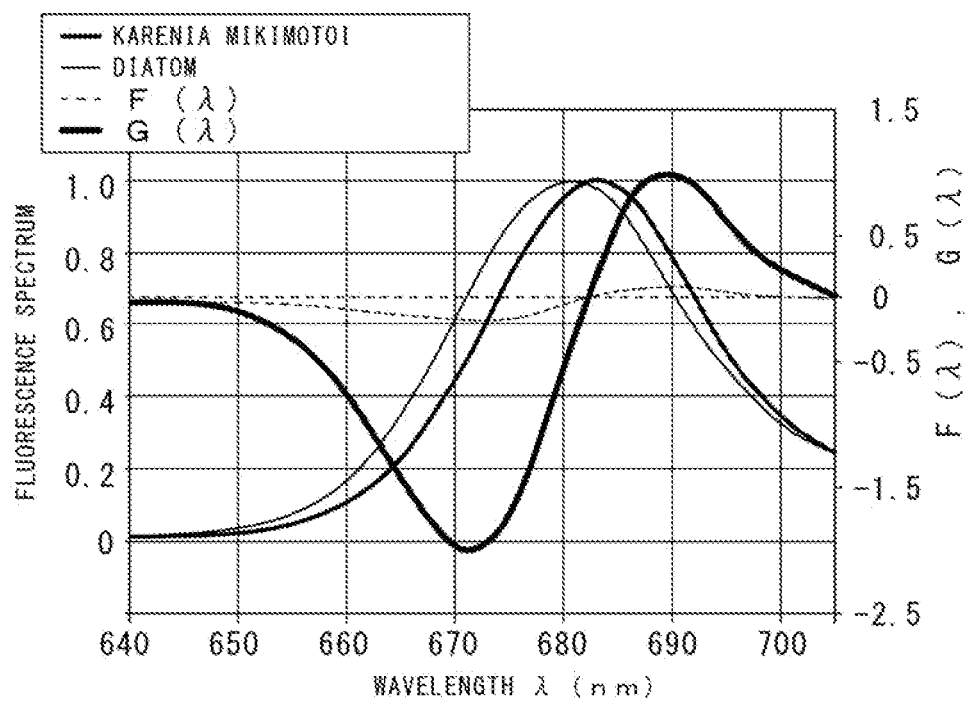
FIG. 5 is a graph explaining how to determine a center wavelength and a width of a wavelength band.

FIG. 5 illustrates the spectrum K(λ) of *Karenia mikimotoi* as an example of the specific species of the phytoplankton, the spectrum D(λ) of a diatom as an example of other species of the phytoplankton, the difference spectrum F(λ), and G(λ) in a case where the width w is 12 nm.

Referring to G(λ), a largest portion and a smallest portion are selected from each other. That is, G(λ) has a minimum value around the center wavelength of 670 nm and a maximum value around the center wavelength of 690 nm. Therefore, a band having a center wavelength of 670 nm and the width w of 12 nm is set as the wavelength band A, and a band having a center wavelength of 690 nm and the width w of 12 nm is set as the wavelength band B.

Note that, in the wavelength band setting method, the width w of a wavelength band is determined based on the light receiving optical filter unit 22 employed in the fluorescence intensity measurement unit 20. However, in a case where a difference between the wavelength bands A and B set by the above-described setting method does not become large, the width w may be reviewed.

Further, as another setting method of setting the wavelength bands A and B, the two selected wavelengths may be selected at positions about 10 nm away from a wavelength where positive and negative are switched, so that a difference between them becomes large, G has a positive value in one of them and G has a negative value in the other, and in consideration of the form of G(λ) obtained above. More specifically, a change in G(λ) is steep near a wavelength (λg) where the positive and negative of G(λ) are switched, and a fluctuation in a measured intensity value becomes large due to, for example, manufacturing variations of the center wavelength and the half peak width of the filter. Therefore, in order to suppress an adverse effect of the above as much as possible, it is effective to set the center wavelength of each filter to a wavelength away from λg to some extent. In this case, since the wavelength where positive and negative are switched is 682 nm, the center wavelength of the wavelength band A may be set to 672 nm, and the center wavelength of the wavelength band B may be set to 692 nm. Roughly, the center wavelength of one wavelength band may be made smaller than the wavelength that is the zero point of F(λ), and the center wavelength of the other wavelength band may be made larger than the wavelength that is the zero point of F(λ).

Furthermore, as still another setting method of setting the wavelength bands A and B, first, as shown in Equations (14) and (15), the spectrum K(λ) and the spectrum D(λ) are integrated by the width w of the wavelength band at the center wavelength λ, and for example, values of 10% of the respective integrated values are set as a K intensity (λ) and a D intensity (λ), respectively. Next, the center wavelength is preferably set in a wavelength range in which an absolute value of G(λ) is larger than the K intensity (λ) and the D intensity (λ). This is a condition based on an idea that G(λ) to be measured is desirably larger by a difference change amount than K (λ) and D (λ) to some extent in a case where an influence of a measurement error is considered.

[Equation 14]

$$K \text{ intensity } (\lambda) = 0.1 \times \int_{\lambda-\frac{w}{2}}^{\lambda+\frac{w}{2}} K(\lambda) d\lambda \quad (14)$$

[Equation 15]

$$D \text{ intensity } (\lambda) = 0.1 \times \int_{\lambda-\frac{w}{2}}^{\lambda+\frac{w}{2}} D(\lambda) d\lambda \quad (15)$$

Figure 6:
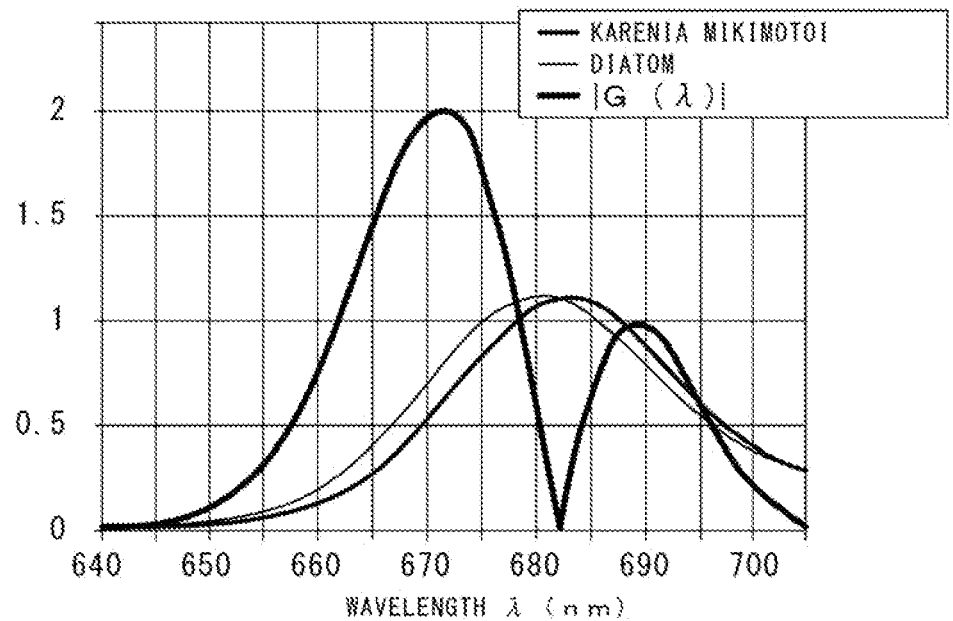
FIG. 6 is a graph explaining how to determine a center wavelength and a width of a wavelength band according to a variation.

FIG. 6 illustrates K intensity (λ), D intensity (λ), and an absolute value of G(λ). That is, as a wavelength band in which an absolute value of G(λ) is larger than the K intensity (λ) and the D intensity (λ), a wavelength band of 645 nm or more and 678 nm or less and a wavelength band of 688 nm or more and 695 nm or less can be selected.

Furthermore, the center wavelength is desirably selected in a range where the K intensity (λ) and the D intensity (λ) are large. For example, it is desirable to set the center wavelength from a wavelength band in which the K intensity (λ) and the D intensity (λ) is 30% or more of the maximum intensity of each of them. Therefore, it is desirable to set the center wavelength from a wavelength band of 665 nm or more and 700 nm or less with reference to FIG. 6.

Therefore, the wavelength band A can be selected from a range in which the center wavelength is 665 nm or more and 678 nm or less, and the wavelength band B can be selected from a range in which the center wavelength is 688 nm or more and 695 nm or less. In this case, for example, the center wavelength of the wavelength band A can be set to 670 nm, and the center wavelength of the wavelength band B can be set to 690 nm.

Figure 7:
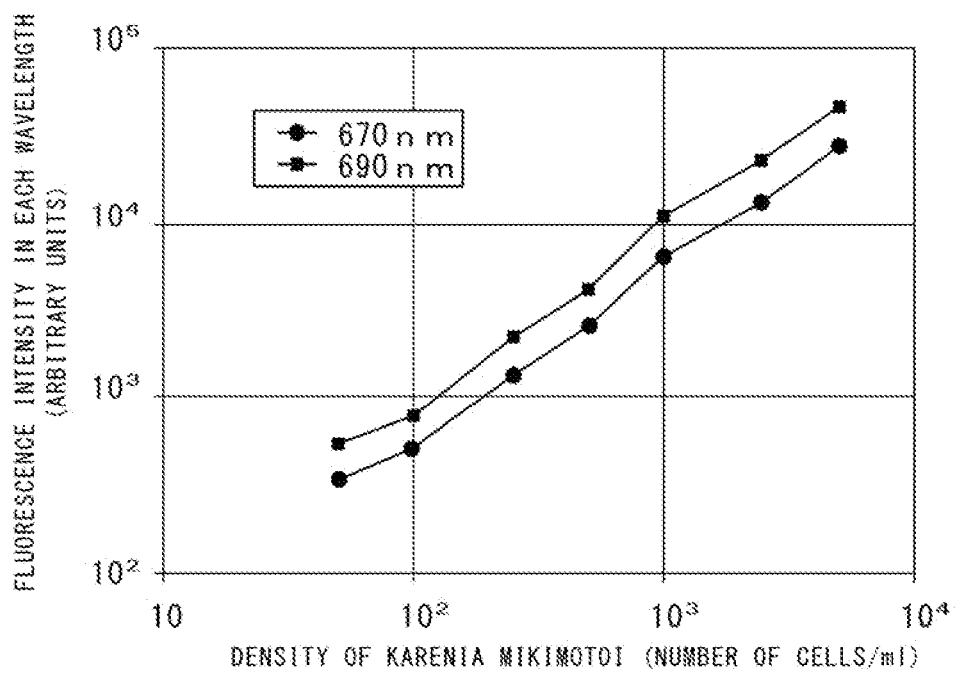
FIG. 7 is a graph showing a relationship between density of specific species of phytoplankton and fluorescence intensity.
Figure 8:
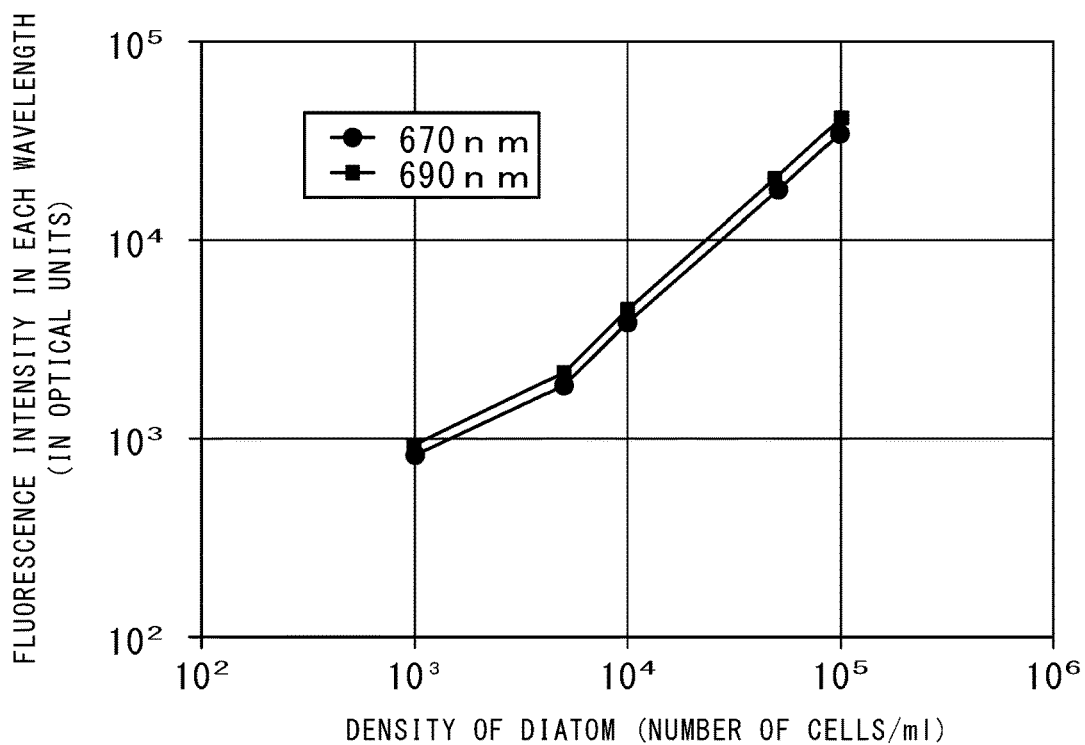
FIG. 8 is a graph showing a relationship between density of another phytoplankton and fluorescence intensity.
Figure 9:
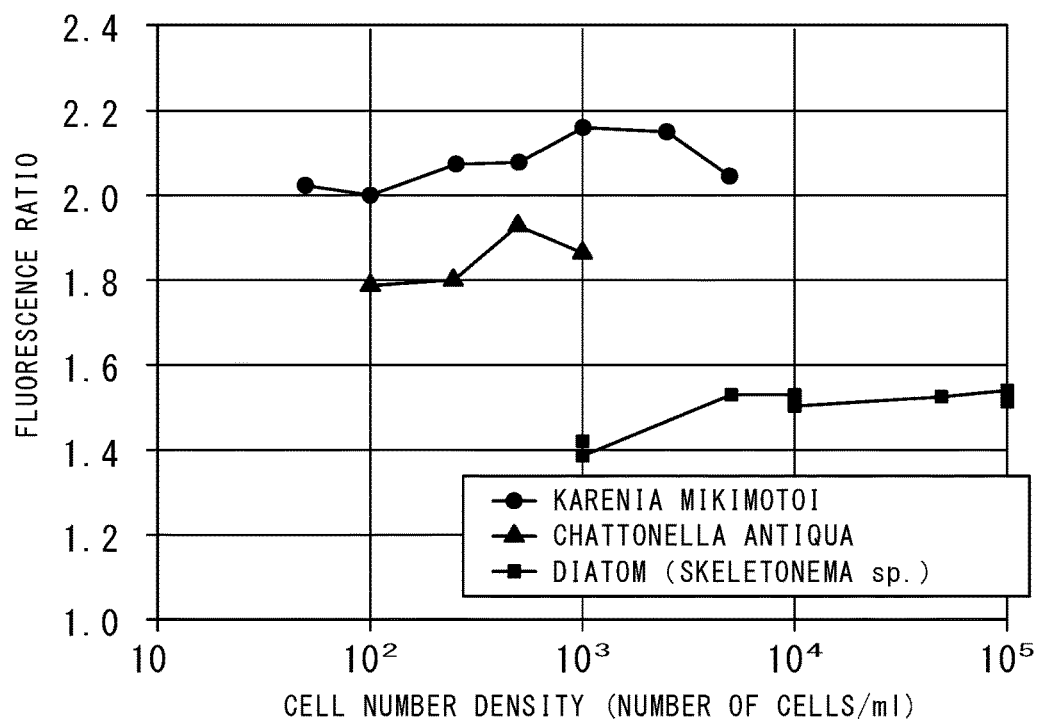
FIG. 9 is a graph showing a relationship between density of phytoplankton and a fluorescence ratio.

The inventor of the present application has confirmed that the fluorescence intensity does not depend on the existing quantity and density of a phytoplankton in a practical number range in a case where consideration is made for the purpose of detecting a sign of a red tide. A specific description will be made with reference to FIGS. 7 to 9. FIG. 7 illustrates fluorescence intensities at 670 nm and 690 nm with respect to the density (the number of cells per 1 ml) of *Karenia mikimotoi* as an example of the specific species of the phytoplankton. Similarly, FIG. 8 illustrates fluorescence intensities at 670 nm and 690 nm with respect to the density (the number of cells per 1 ml) of a diatom as an example of other species of the phytoplankton. Further, FIG. 9 illustrates a fluorescence ratio (a ratio of a fluorescence intensity at 690 nm to a fluorescence intensity at 670 nm) of *Karenia mikimotoi* and *Chattonella antiqua* as the specific species of the phytoplankton and a diatom as other species of the phytoplankton.

As illustrated in FIGS. 7 and 8, the fluorescence intensity of a phytoplankton increases in proportion as the density increases, and does not tend to saturate at a constant value. Further, as illustrated in FIG. 9, a fluorescence ratio of a phytoplankton is substantially constant regardless of the density. Therefore, it is confirmed that the fluorescence intensity of a phytoplankton does not depend on the number and density of the phytoplankton, and the above calculation algorithm is established.

FIGS. 10A, 10B, and 10C illustrate, for an analysis sample analyzed over a water depth of 0 m to 9 m in a sampling target location, and using *Karenia mikimotoi* as the specific species of the phytoplankton as an analysis target, the existing quantity of *Karenia mikimotoi* in the analysis sample is shown for each water depth by a measured density obtained by counting with a microscope and an estimated density based on the existing quantity calculated by the calculation unit 32.

Note that the calculation of the existing quantity K of the specific species of the phytoplankton by the calculation unit 32 is performed in two cases, a case where the intensity ratio $r_d$ of other species of plankton is fixed at an initial value and a case where the intensity ratio $r_d$ of other species of plankton is updated every week. The case where the intensity ratio $r_d$ of other species of plankton is constant at an initial value is indicated by a thin line, and the case where the intensity ratio $r_d$ of other species of plankton is updated every week is indicated by a thick line. Further, the calculation unit 32 calculates the constant number α in Equation (9) as 0.62 from an actual measured value using *Karenia mikimotoi* as the specific species of the phytoplankton as described above.

Further, sampling of a sample is performed every week, FIG. 10(*a*) illustrates an analysis result at the start of analysis (Week 0), FIG. 10(*b*) illustrates an analysis result after one week elapses from the start of analysis (Week 1), and FIG. 10(*c*) illustrates an analysis result after two weeks elapses from the start of analysis (Week 2).

Further, in a case where the intensity ratio $r_d$ of other species of plankton is updated, in Week 1, the intensity ratio $r_d$ of other species of plankton is replaced with the intensity ratio $r_d$ of other species of plankton obtained from Equation (9) based on the existing quantity K actually measured in Week 0 and I and r measured in the calculation apparatus 1. Similarly, in Week 2, the intensity ratio $r_d$ of other species of plankton is replaced with the intensity ratio $r_d$ of other species of plankton obtained from Equation (9) based on an actual measurement result of Week 1. For this reason, in Week 0 illustrated in FIG. 10(*a*), the intensity ratio $r_d$ of other species of plankton remains at the initial value calculated on the basis of the reference sample, and the same $r_d$ is used for both the case where the intensity ratio $r_d$ of other species of plankton is fixed and the case where the intensity ratio $r_d$ of other species of plankton is updated.

As illustrated in FIGS. 10A, 10B and 10C, as time elapses from the start of analysis, a difference from the measured density increases in the case where the intensity ratio $r_d$ of other species of plankton is fixed, whereas the difference from the measured density is small in the case where the intensity ratio $r_d$ of other species of plankton is updated. Therefore, by periodically updating the intensity ratio $r_d$ of other species of plankton in accordance with a change in the composition of other species of the phytoplankton existing in the sampling target location, an abundance of the specific species of the phytoplankton can be calculated with high accuracy.

Note that, in the calculation by the calculation unit 32, the constant number α in Equation (9) is constant at 0.62. However, in actuality, the constant number α is defined by Equation (8) and may take a positive value of one or less. From Equation (8), it is obvious that a is positive, and since a fluorescence spectrum of the specific species of the phytoplankton is shifted to the longer wavelength side, a is one or less. In view of the above, in FIGS. 10A, 10B, and 10C, a calculation results when the constant number α is changed to 0.1 and 1.0 are also indicated by a broken line on the assumption of the calculation of an abundance of the specific species of the phytoplankton in the case where the intensity ratio $r_d$ of other species of plankton is updated.

As can be seen from each diagram in FIGS. 10A, 10B, and 10C, even if the constant number α changes, the degree of influence on a result of the existing quantity of the specific species of the phytoplankton is small. In particular, the degree of influence on the calculation result of the existing quantity of the specific species of the phytoplankton is smaller in the case where the constant number α is changed on the basis of the intensity ratio $r_d$ of other species of plankton that is updated than in the case where the intensity ratio $r_d$ of other species plankton is a fixed value. Therefore, it is understood that the constant number α may be a constant value.

In the above embodiment, the existing quantity K is calculated as an abundance of the specific species of the phytoplankton. However, instead of this, the existing quantity may be converted into an index value and expressed as the abundance. Therefore, the abundance includes not only a quantitative existing quantity but also a qualitative index or expression. For example, the existing quantity K of the specific species of the phytoplankton may be converted into an index value y distributed between an upper limit value and a lower limit value of h using a monotonic function h(K), so that a relative relationship of the existing quantity is understood.

Further, on the basis of the existing quantity K or a value of the converted index value y, the existing quantity may be expressed in a statistical expression or a color, a character, a sentence, a figure, a symbol, a photograph, or the like determined for each value range so that the degree of the existing quantity can be understood. Specifically, the finite index value y can be obtained by substituting, for example, the existing quantity K or an estimated density of the specific species of the phytoplankton into x using a monotonically increasing function expressed by Equation (16).

[Equation 16]

$$y = \frac{1}{1 + e^{-ax}} \tag{16}$$

The abundance may be expressed as described below according to the obtained index value y.

For example, the abundance may be expressed as a number, and in this case, for example, may be expressed as a continuous value from 0 to 10 or a discrete value expressing the degree of caution corresponding to the value of y.

Further, the abundance may be expressed by a color, and in this case, for example, may be expressed by using "red" when y is equal to or more than a first value, "yellow" when y is within a range of the first value to a second value, and "blue" when y is equal to or less than the second value. Further, an abundance of the specific species of the phytoplankton may be expressed in a warm colors as the abundance is larger, and expressed in a cool colors as the abundance is smaller.

Further, the abundance may be expressed by a word, and in this case, for example, may be expressed by using words such as "Waning" when y is equal to or more than a first value, "Caution" when y is within a range of the first value to a second value, and "Normal" when y is equal to or less than the second value.

Further, the abundance may be expressed by a figure, and in this case, for example, may be expressed by a figure or illustration such as "Illustration 1" when y is equal to or more than a first value, "Illustration 2" when y is within a range of the first value to a second value, and "Illustration 3" when y is equal to or less than the second value.

Further, the abundance may be expressed by a sound, and in this case, for example, may be expressed by using a difference in sounds, such as "Sound Pattern 1" when y is equal to or more than a first value, "Sound Pattern 2" when y is within a range of the first value to a second value, and "Sound Pattern 3" when y is equal to or less than the second value.

Note that the intensity ratio $r_d$ of other species of plankton may be obtained by replacing the existing quantity K with the index value y on the basis of Equation (9). According to Equation (9) into which the intensity ratio $r_d$ of other species of plankton obtained in this manner is substituted, the index value y of the analysis sample is directly obtained from the total fluorescence intensity I and the intensity ratio r calculated for the analysis sample. For example, the existing quantity of the specific species of the phytoplankton that may exist in the analysis sample may be estimated by looking at the color of the analysis sample, an index value y may be set based on the existing quantity, and the set value y may be used as the abundance K, so that the intensity ratio $r_d$ of other species of plankton satisfying them is calculated.

Further, in the above embodiment, the case where the calculation unit 32 and the sign detection unit 33 are integrated with the control device 30 of the calculation apparatus 1 is described as an example. However, the present invention is not limited thereto, and the configuration may be such that a calculation system has a part configured as a separate body. For example, while the drive unit 31 may be arranged in the sampling target location together with the light emitting element 11 and the light receiving element 21, a measured intensity may be transmitted to the calculation unit 32 located in a remote location (for example, a landside) away from the sampling target location by a communicating means (not illustrated). Similarly, the sign detection unit 33 may be provided in a remote location together with the calculation unit 33.

Note that the present invention is not limited to the configuration described in the above embodiment, and various changes can be made.

DESCRIPTION OF SYMBOLS

1 Calculation apparatus for calculating abundance of specific species of phytoplankton
10 Excitation light generation unit
11 Light emitting element
12 Light sending optical filter unit
20 Fluorescence intensity measurement unit
21 Light receiving element
22 Light receiving optical filter unit
30 Control device
31 Drive unit
32 Calculation unit
33 Sign detection unit
I Total fluorescence intensity
I670 Wavelength band A fluorescence intensity
I690 Wavelength band B fluorescence intensity
r Intensity ratio
Ik Unit fluorescence intensity of specific species of plankton
Ik670 Unit fluorescence intensity in wavelength band A of specific species of plankton
Ik690 Unit fluorescence intensity in wavelength band B of specific species of plankton
$r_k$ Intensity ratio of specific species of plankton
K Existing quantity of specific species of phytoplankton
Id Unit fluorescence intensity for other species of plankton
Id670 Unit fluorescence intensity in wavelength band A of other species of plankton
Id690 Unit fluorescence intensity in wavelength band B of other species of plankton
$r_d$ Intensity ratio of other species of plankton
D Existing quantity of other species of phytoplankton
α Constant number
$I_0$ Reference sample total fluorescence intensity
$r_0$ Reference sample intensity ratio
$K_0$ Reference abundance

The invention claimed is:

1. A method for calculating an abundance of specific species of phytoplankton, the method comprising:
    irradiating a reference sample containing a phytoplankton group with excitation light, the phytoplankton group containing a plurality of kinds of phytoplankton, the plurality of kinds of phytoplankton possibly including specific species of phytoplankton, and the specific species of the phytoplankton emitting fluorescence by absorbing the excitation light;
    measuring an intensity of the fluorescence emitted from the reference sample in each of two wavelength bands and calculating a reference sample intensity ratio that is a ratio of intensities of these two;
    measuring a reference sample total fluorescence intensity that is an intensity in a substantially entire wavelength band of the fluorescence emitted from the reference sample;
    counting a reference abundance of the specific species of the phytoplankton contained in the reference sample;
    calculating an other species plankton intensity ratio, that is a ratio of intensities in the two wavelength bands of the fluorescence emitted from other species of a phytoplankton other than the specific species of the phytoplankton in the phytoplankton group, based on the reference sample intensity ratio, the reference sample total fluorescence intensity, and the reference abundance;
    irradiating an analysis sample, which is expected to have similarity with the reference sample with respect to composition of the phytoplankton group, with excitation light;
    measuring an intensity of the fluorescence emitted from the analysis sample in each of the two wavelength bands and calculating an intensity ratio that is a ratio of intensities of these two;
    measuring a total fluorescence intensity that is an intensity in a substantially entire wavelength band of the fluorescence emitted from the analysis sample; and
    calculating an abundance of the specific species of the phytoplankton that may be contained in the analysis sample based on the other species plankton intensity ratio, the intensity ratio, and the total fluorescence intensity.

2. The method for calculating the abundance of the specific species of the phytoplankton according to claim 1, wherein
    the abundance is an existing quantity of the specific species of the phytoplankton.

3. The method for calculating the abundance of the specific species of the phytoplankton according to claim 1, wherein
    the abundance is expressed as an index based on an existing quantity of the specific species of the phytoplankton.

4. The method for calculating the abundance of the specific species of the phytoplankton according to claim 3, wherein
the index is represented by an expression indicating a degree of the existing quantity.

5. The method for calculating the abundance of the specific species of the phytoplankton according to claim 1, further comprising:
calculating the other species plankton intensity ratio based on a plurality of sets of the reference sample intensity ratio, the reference sample total fluorescence intensity, and the reference abundance, which are measured or calculated for each of a plurality of the reference samples.

6. The method for calculating the abundance of the specific species of the phytoplankton according to claim 1, further comprising:
updating the other species plankton intensity ratio over time.

7. A sign detection method for red tide occurrence caused by specific species of phytoplankton, the specific species of the phytoplankton being possibly a cause of red tide occurrence, the sign detection method comprising:
detecting a sign of red tide occurrence based on the abundance calculated by the method for calculating the abundance of the specific species of the phytoplankton according to claim 1.

8. An apparatus for calculating an abundance of the specific species of the phytoplankton, the apparatus comprising:
an excitation light generation unit that irradiates a reference sample containing a phytoplankton group with excitation light, the phytoplankton group containing a plurality of kinds of phytoplankton, the plurality of kinds of phytoplankton possibly including the specific species of the phytoplankton, and the specific species of the phytoplankton emitting fluorescence by absorbing the excitation light;
a fluorescence intensity measurement unit that measures a reference sample wavelength band fluorescence intensity that is an intensity in each of two wavelength bands and a reference sample total fluorescence intensity that is an intensity in a substantially entire wavelength band; and
a calculation unit that calculates a reference sample intensity ratio that is a ratio of the two reference sample wavelength band fluorescence intensities and calculates an other species plankton intensity ratio that is a ratio of intensities in each of the two wavelength bands of the fluorescence emitted from other species of phytoplankton other than the specific species of the phytoplankton in the phytoplankton group based on the reference sample intensity ratio, the reference sample total fluorescence intensity, and a reference abundance counted in advance in the specific species of the phytoplankton contained in the reference sample, wherein
the excitation light generation unit irradiates an analysis sample, which is expected to have similarity with the reference sample with respect to composition of the phytoplankton group, with excitation light,
the fluorescence intensity measurement unit measures a wavelength band fluorescence intensity that is an intensity in each of the two wavelength bands of the fluorescence emitted from the analysis sample and a total fluorescence intensity that is an intensity in a substantially entire wavelength band of the fluorescence emitted from the analysis sample, and
the calculation unit calculates an intensity ratio that is a ratio of two of the wavelength band fluorescence intensities, and calculates an abundance of the specific species of the phytoplankton that may be contained in the analysis sample based on the other species plankton intensity ratio, the intensity ratio, and the total fluorescence intensity.

9. A sign detection apparatus for red tide occurrence caused by specific species of phytoplankton, the sign detection apparatus comprising:
a sign detection unit that detects a sign of red tide occurrence caused by the specific species of the phytoplankton based on the abundance of the specific species of the phytoplankton calculated by the apparatus for calculating an abundance of the specific species of the phytoplankton according to claim 8.

* * * * *